United States Patent [19]
Eibl et al.

[11] Patent Number: 5,804,159
[45] Date of Patent: Sep. 8, 1998

[54] ANTIPLASMA ANIMAL MODEL

[75] Inventors: Johann Eibl, Vienna; Peter Turecek, Klosterneuburg Weidling; Hans Peter Schwarz, Vienna, all of Austria

[73] Assignee: Immuno Aktiengesellschaft, Vienna, Austria

[21] Appl. No.: 663,031

[22] Filed: Jun. 7, 1996

[30] Foreign Application Priority Data

Jun. 9, 1995 [AT] Austria ............................ 987/95

[51] Int. Cl.$^6$ .......................... A61K 48/00; C12N 15/63; C07K 16/00
[52] U.S. Cl. .................... 424/9.1; 800/2; 424/9.2; 424/130.1; 435/7.2; 435/375; 435/172.3
[58] Field of Search ................. 800/2; 435/7.2, 435/375, 172.3; 530/387.1; 514/2; 424/130.1, 178.1, 9.1

[56] References Cited

FOREIGN PATENT DOCUMENTS

WO 95/01570  1/1995  WIPO .

OTHER PUBLICATIONS

O'Brien et al., J. Clin. Invest., 82: 206–211 (Jul. 1988).
Marion M. Bradford, Protein Assay by Dye Binding, pp. 249–254.
Giles et al., Blood, 60(3): 727–730 (Sep. 1982).
Novak et al., British Journal of Haematology 69: 371–378 (1988).
Ruggeri et al., Blood, 57(6): 1140–1143 (Jun. 1981).
Aihara et al., Thrombosis & Haemostasis, 55(2): 263–267 (1980).
The Merk Manual or Diagnosis and Therapy, Ed. Berkow et al., 16th edition, Merck & Co., Inc., Rahway, N.J., 1992.
Brinkhous et al. "von Willebrand Factor and Animal Models: Contributions to Gene Therpy, Thrombotic Thrombocytopenic Purpura, and Coronary Artery Thrombosis," Mayo Clin Proc, vol. 66:733–742, 1991.
Table of Proteins of Human Blood Plasma, Reagents of Behringwerke, Schultze and Heremans, Elsevier, 1966.
Tiarks et al. "Hypothesis for the Control of Clotting Factor VIII Inhibitory Antibodies by Decreasing Potency of Helper T–cell–Recognized Epitopes in Factor VIII" Scand. J. Immunol., vol. 36: 653–660, 1992.
Carmona et al., Thrombosis Reserach 63: 73–84 (1991).
Gawryl et al., Blood 60(5): 1103–1109 (1982).

*Primary Examiner*—Jasemine C. Chambers
*Assistant Examiner*—Karen M. Hauda
*Attorney, Agent, or Firm*—Foley & Lardner

[57] ABSTRACT

There is disclosed an anti-plasma antibody preparation for treatment of a mammal, which preparation is capable of directly or indirectly inhibiting and/or eliminating several blood factors, a method of producing such a preparation and a method of evaluating substances for treating clotting disorders by using said anti-plasma antibody preparation. There is further disclosed a method of determining the bleeding characteristics of a mammal.

3 Claims, 7 Drawing Sheets

*FIG. 5*
MOUSE

ANTIPLASMA ANIMAL MODEL

BACKGROUND OF THE INVENTION

The present invention relates to an anti-plasma and antibody preparation, a method for the preparation thereof as well as the use of these preparations. Furthermore, the invention relates to a method of evaluating substances for the treatment of blood coagulation disorders in an animal model together with a method of determining the bleeding characteristics in a mammal.

To evaluate substances with respect to their suitabilty for the treatment of blood coagulation disorders it is necessary to provide a suitable animal model which mimics the characteristics of the corresponding clinical syndromes in man as closely as possible.

Hitherto hemophilic dogs have, for instance, been used for the pre-clinical examination of potential pharmaceuticals for the treatment of hemophilia, which dogs have a genetic defect similar to that of hemophilic human beings. The breeding conditions for these hemophilic dogs are, however, extremely complicated and labor-intensive, since the dogs are extremely prone to hemorrhaging on account of their genetic defect. Moreover, the number of available animals is determined by the probability of the occurrence of the hereditary clotting defect.

In J. Clin. Invest. 82 (1988), 206–211, it has been described that an animal model for hemophilia A can be obtained by infusion of human anti-factor VIII antibody in normal rabbits. In this model, the factor VIII concentration in the blood of the rabbits could be lowered within 30 minutes from the normal value to below the detection limit on account of a high-titer human anti-factor VIII antibody. The thus prepared animals exhibited a large loss of blood when bleeding was induced at the artery of the ear. Such pronounced arterial bleeding is, however, not typical for the bleeding situation in hemophiliacs, since there the bleeding rather corresponds to an arteriovenous seeping hemorrhage.

In WO 95/01570 this animal model has been further developed in that antibodies against the light chain of the human or porcine factor VIII:C molecule were produced in a first animal and subsequently a temporary hemophilia was induced in a second animal by means of the purified monospecific antibody obtained. Thus, the specificity of the antibodies was considerably restricted (to merely the light chain of the factor VIII:C molecule). As a consequence animals were obtained which have very high inhibitor titers (between 17 and 42 Bethesda units), yet the induced hemophilic condition lasted only very shortly in these animals, and therefor the determination of the cuticle bleeding time for evaluating the test substances already had to be started after 40 minutes and not, as is preferred, after 60 minutes.

The animal model described in Wo 95/01570 based on monospecific antibodies also is comparable to the actual conditions found in hemophilic patients to a limited extent only, because a wide spectrum of inhibitor antibodies usually occurs in such patients and not merely antibodies which are directed against a certain protein chain or a certain epitope. The short period of time during which the animals according to WO 95/01570 are in a state suitable for evaluating the test substances often is not sufficient for comprehensive test series, and thus falsified results may be obtained, in particular as concerns the end of bleeding, which may interfere with the decline of the induced hemophilia in the test animal.

Therefore it is the object of the present invention to provide an improved test system for substances for the treatment of clotting disorders which reflects the clinical situation in the patient as closely to practice as possible and whose evaluation results are thus very reliably applicable.

SUMMARY OF THE INVENTION

According to the invention, this object is achieved by an anti-plasma antibody preparation for treatment of a mammal, which preparation can directly or indirectly inhibit and/or eliminate several blood factors.

Treatment of a mammal with the preparation according to the invention induces a temporary clotting disorder in the treated mammal, which, on account of the specificity and effect regarding several blood factors reflects true-to-practice the condition in patients suffering from clotting disorders, such as hemophilia, immuninhibitor hemophilia, von Willebrand disease (von Willebrand-Jürgens syndrome) or in patients suffering from a deficiency of vitamin K-dependent blood factors. In particular, the system according to the invention is suitable to simulate patients who have developed antibodies which inhibit the effect of blood factors, such as, e.g. von Willebrand factor or factor VIII.

A characteristic feature of the preparation according to the invention is that, in contrast to the prior art, not only a monospecific antibody directed against one blood coagulation factor only, or only against a specific epitope of this blood coagulation factor is used to induce the blood clotting disorder, but that the preparation acts on several blood coagulation factors.

This effect can be obtained in that the preparation either comprises antibodies against a preferably human blood factor which itself directly inhibits or eliminates other blood factors, or in that the preparation is obtained by immunization against a plurality of the most varying epitopes, mostly of different blood factors.

A preferred example of the first instance is a preparation comprising antibodies against human von Willebrand factor, which antibody cross-reacts directly with the animal-derived von Willebrand factor and indirectly destabilizes the animal-derived factor VIII, thus eliminating the latter. Preferred examples of the second instance are a preparation comprising antibodies against factor VIII/von Willebrand-factor-complex or against vitamin K-dependent blood factors, e.g. factors of the prothrombin complex.

Further preferred examples relate to preparations with antibodies against procoagulants (blood coagulation factors II, V, VII, IX, X, XI, XII, prekallikrein, kininogen and tissue factor), but also preparations with antibodies against anticoagulants (protein C, protein S, antithrombin III, heparin cofactor II), clot structure factors (fibrinogen and factor XIII), fibrinolysis factors (plasminogen, t-PA, PAI-1 and $\alpha_2$-plasmin inhibitor) and phospholipids.

The suitability of the antibody preparation according to the invention for the preparation of a test animal as animal model can be judged on the basis of various tests. Preferably, an in vitro-test is carried out in which the antibody preparation is incubated with a blood or plasma sample of a test animal, and the inhibition or elimination, respectively, of the blood factors is determined. The desired effect of changed bleeding characteristics can also be shown in a test animal in vivo by inducing a control bleed. It is preferred that the induced effect should last for a longer period of time, at least for several hours. Yet a selection criterion for the preparation according to the invention is not only its efficacy in vitro or in vivo, but also a high antibody titer, e.g. more than 300 BU/ml, for antibodies against factor VIII.

What is always important is that the preparation comprises polyclonal, polyspecific antibodies with as broad an epitope spectrum as possible, which antibodies cross-react with the corresponding antigens in the test animal. The administration of a preparation according to the invention to a test animal thus not only allows for a qualitative similarity to the human blood clotting disorders, but, surprisingly the condition of the induced blood clotting disorder in the animal also lasts for a longer period of time. As a consequence, the administration of the test substances for eliminating the blood clotting disorder can be reliably evaluated over a longer period of time without having to take into account the possibility that a return to the normal condition in the animal will falsify the evaluation results.

While in the animal model with monospecifically induced factor VIII deficiency according to WO 95/01570, the bleeding already stops in 40% of the animals (two out of five) after 30 minutes despite a high inhibitor titer, with the preparation according to the invention hemorrhaging periods of 30 minutes (90 minutes from the induction with the antibody preparation) or more, up to the maximum hemorrhaging time possible can be attained without any problem.

The preparation according to the invention can, e.g., be obtained by immunizing a mammal with plasma, preferably with human plasma, or with a plasma fraction or with the recombinant equivalent thereof, recovering the antiplasma or antiserum and subsequently absorbing one or several antibodies of the antiplasma or the antiserum so that the preparation will contain only such functional antibodies which can selectively functionally inhibit and/or eliminate one or several selected blood factors in a mammal.

In a preferred embodiment of the present invention, immunization is achieved with factor VIII/von Willebrand complex, and the absorption of factor VIII antibodies is ensured by the addition of factor VIII, in particular of a factor VIII concentrate. With a thus prepared preparation, the clinical situation of the von Willebrand-Jürgens syndrome or other bleeding inclinations related to hemophilia can be exactly simulated in test animals, so that in such a model substances having a clinically relevant meaning can be tested for their efficacy for the therapy of hemorrhagic dietheses occurring therein. Likewise, by adding a von Willebrand factor preparation to the preparation, the specific absorption of the von Willebrand factor antibodies may occur under suitable conditions, whereby antibodies against factor VIII become effective.

A method of preparing the preparation according to the invention is characterized by the following steps:
- immunizing a mammal with a plasma or a plasma fraction or with the recombinant equivalent thereof,
- recovery of the antiplasma or antiserum,
- optionally, preparing the antibody fraction from the antiplasma or antiserum,
- optionally absorbing one or several antibodies by contacting the antibodies with certain proteins, and
- formulating a preparation suitable for infusion into a mammal.

Preferred plasma fractions for immunization are preparations containing factor VIII/von Willebrand complex, von Willebrand factor, prothrombin complex, blood clotting factor preparations etc. The substances used for the immunization preferably are of human origin, since the substances to be evaluated are intended for the treatment of humans. If immunizing material of animal origin is used, care must be taken that there is a sufficient homology to the human epitopes.

Recovery of the antiplasma or antiserum may be effected in a known manner, i.e. by plasmapheresis, plasma separation (membrane filtration, centrifugation, cell separation), precipitation etc.

An antiplasma is defined as a plasma which can be obtained by immunizing a mammal or human with antigens. It is obtained by separating the corpuscular components from whole blood. An example of an antiplasma is an inhibitor plasma. An antiserum is also obtained from an immunized mammal or human, yet therein the liquid phase of the blood is recovered after clotting has taken place.

Development of the antibody fraction may consist of a simple purification, yet in some instances it may be suitable to use a comprehensive purification of the antibodies, particularly if the test animal in which the blood clotting disorder is to be induced is sensitive to contaminations or unspecific antibodies, respectively. Furthermore, working up may comprise steps in which substances that may impair the effect of the antibodies (e.g. blood factors of the immunized animal) are inactivated in the preparation or removed therefrom, while the substantially more stable antibodies remain unaffected. This step may, e.g., have the form of a heat treatment, preferably carried out for a period of time of from 1 minute to several hours at a temperature of from 40° to 80° C.

Also certain affinity materials are suitable for the selective removal of interfering substances from the antibody fraction.

To cause a precisely defined syndrome of the induced blood clotting disorders in the test animals it may also be necessary to make the prepared inhibitor plasma preparation containing the anti-plasma antibodies specific for a certain blood factor and/or to exclude a cross-reactivity with certain other blood factors which may be contained in the material for immunization (immunizing antigen). To this end, an absorption step may be provided in the preparation method, in which one or several antibodies or groups of antibodies are absorbed by bringing them into contact with certain proteins. Absorption of certain antibodies may also occur in vivo, i.e. in the test animal, e.g. by administering certain antigens to the test animal.

Finishing to a pharmaceutically acceptable preparation suitable for infusion in a mammal is also performed in a known manner and is dependent in each case on the type of mammal to be infused.

Preferred mammals in which immunization is carried out comprise sheep, goats, cows, pigs, rabbits, guinea pigs, horses, rats and mice. Preferred mammals in which the blood clotting disorder is induced are also the above-mentioned ones, particularly leporidae and rodents, such as rabbits, rats and mice.

In a further aspect the present invention relates to the use of anti-plasma antibodies (e.g. in an infusion preparation) for the treatment of a mammal as a model for a deficiency of blood factors by functionally inhibiting and/or eliminating several blood factors, so that the clotting time in vitro or ex vivo or the bleeding characteristics in the mammal are changed. Optionally, antibodies against certain blood factors are absorbed in vivo by administering the blood factors to the animal.

A preferred application thus is characterised in that by re-substitution with one or several blood factors, the changed clotting time and bleeding characteristics are merely dependent on a deficiency of that blood factor or blood factors which have not been substituted.

To provide a practical handling of the system according to the invention, the invention in a further aspect relates to a kit for preparing a mammal as an animal model, which kit comprises
 a) an anti-plasma antibody preparation according to the invention, and b) an infusion device for a mammal.

Optionally, also c) proteins for absorption of certain antibodies may be comprised in the kit.

According to a further aspect, the present invention relates to a method of determining the bleeding characteristics of a mammal, characterised by the steps of

- inducing a bleeding site in a mammal,
- collecting blood fractions from said bleeding site,
- determining the hemoglobin content of the collected blood fractions, and
- determining the accumulated blood loss and/or the bleeding kinetics.

Hitherto, bleeding characteristics have been examined by methods which enable only a rough estimate of the course of bleeding, and which were very error-prone, respectively. In the prior art, e.g., bleeding characteristics were determined by merely observing the duration of bleeding or the end of bleeding was determined by continuous blotting on a filter paper (end=no traces of blood recognizable on the filter paper).. In a different method, the blood exuded was collected over the entire time and quantitated e.g. by weighing, evaporation losses always having to be taken into account.

According to the present invention, however, the blood fractions emerging from the induced wound are preferably continuously collected over the entire period of bleeding, preferably by applying the blood to suitable absorption materials and subsequently determining the hemoglobin content of the blood fractions. Filter materials or cotton plugs have, e.g., proved to be suitable absorption materials. It is important that they are able to quantitatively accumulate the blood and do not negatively affect the hemoglobin determination. When collecting the blood fractions with absorption materials, care must be taken that no capillary effect towards the wound is created, whereby a blood clot forming could be damaged.

By determining the hemoglobin, which preferably is performed spectrophotometrically, the method according to the invention becomes independent of evaporation losses and thus may yield an unfalsified and quantitatively exact illustration of the course of bleeding.

The induced bleeding preferably is arteriovenous bleeding and is caused by injuring the extremities of the test animal, e.g. by a cut of the tip of the tail or by cutting the claws (cuticle bleeding).

The determination of bleeding characteristics for the animal model induced with the preparations according to the invention is, of course, not limited to the hemoglobin method, but may be carried out with any determination method disclosed in the prior art.

A further aspect of the present invention relates to a method of evaluating substances for treating clotting disorders and comprising the following steps:

- treating a mammal with an anti-plasma antibody preparation according to the invention so as to induce a clotting disorder in the mammal,
- administering the substance to be evaluated to the mammal, and
- determining one or several clotting parameters and/or the change in the bleeding characteristics of the mammal by the substance to be evaluated, this determination optionally being not effected or being effected only partially on the animal itself, but being effected by separate examinations.

A clotting parameter is defined as a parameter determined as a statement on the status of coagulation. The determination of a clotting parameter is effected according to known methods. For instance, a series of in vitro examinations for testing blood clotting factors or fibrinolysis factors and their effect in blood or plasma samples are known.

In the method according to the invention, the bleeding characteristics of a mammal with induced blood clotting disorder are compared to the bleeding characteristics of a mammal with induced blood clotting disorder which has received the compound to be tested. It is assayed to what extent the substance to be tested can counteract the induced blood clotting disorder. The determination of the change in the bleeding characteristics is realized most simply by comparing the bleeding times of animals which have received the substance to be evaluated, with those of animals in which the clotting disorder has been induced only. More complicated determinations comprise a comparison of the bleeding behaviour, a comparison of the volumes of blood emerged from the wound, bleeding kinetics etc..

The substance to be tested may be tested for prevention or therapy, yet generally it is administered prior or after induction of the clotting disorder (preferably either simultaneously with the causing of the bleeding or as soon as the infused substance has been distributed in the circulatory system).

After having caused the clotting disorder, preferably a control bleed is induced in the animal, e.g. by cutting a claw. When the bleeding characteristics appear changed as expected, the animal may be Judged as suitable for further examinations.

It is important to emphasize that the determination of the change in the bleeding characteristics is not effected on the mammal itself or is only partially effected on the mammal, yet at least as regards the determination of blood fractions or the determination of the clotting parameters, these are carried out in separate laboratory tests. These laboratory tests may be hemoglobin assays, volume and weight determinations, respectively, or like examinations. Further examinations relate to the evaluation of the clotting system in blood samples by known methods, e.g. aPTT, prothrombin time, determination of clotting factors etc..

In a further aspect the present invention also relates to a mammal having a blood clotting disorder induced by an anti-plasma antibody preparation according to the invention, the induced blood clotting disorder preferably being an induced von Willebrand-Jürgens syndrome or another hemorrhaging inclination related to hemophilia.

The anti-plasma antibody preparations according to the invention can be used not only to induce a blood clotting disorder in a mammal, but also directly for preparing a pharmaceutical preparation for the prevention and treatment of syndromes involving the occurrence of undesiredly high activities of blood factors, e.g. an anti-human von Willebrand factor preparation for the prevention and treatment of hemolytic or uremic syndrome, adult respiratory distress syndrome (ARDS) or arteriosclerosis. These conditions are exemplary for those involving thrombocyte aggregation due to abnormal von Willebrand factor acitivities.

BRIEF DESSCRIPTION OF THE DRAWINGS

The invention will now be described in more detail by way of the following examples and the drawing figures, to which, however, it shall not be restricted.

DESCRIPTION OF THE PREFERRED EMBODIMENTS

EXAMPLES

EXAMPLE 1

Recovery of anti-vWF inhibitor plasma

A goat (50–60 kg body weight, 1.5 years old) is immunized with von Willebrand factor/factor VIII-complex. The von Willebrand factor/factor VIII complex is recovered as follows:

1 g of cryoprecipitate is dissolved in 35 ml of a Tris/lysin buffered NaCl solution (85 mM). Proteins of the prothrombin complex are removed by adsorption on $AlOH_3$ and $BaSO_4$. To this end, the solution containing von Willebrand factor/factor VIII is incubated with 0.1 % by weight of $AlOH_3$ for one hour at 22° C. Subsequently, the $AlOH_3$ protein complex is separated by centrifugation. The recovered supernatant is further incubated with 0.1% by weight of $BaSO_4$ under stirring, and the $BaSO_4$ protein complex is again separated by centrifugation. Subsequently, the supernatant is adjusted to pH 6.8 and purified by chromatography over Q-Sepharose® FF (Pharmacia). The von Willebrand factor complex is adsorbed on the gel packed in a column; non-binding proteins are removed by washing with 4 column volumes of the starting buffer. Elution of the protein fraction is carried out with a buffer (50 mM Tris/HCl, 500 mM NaCl, pH 6.8). The eluate obtained is diluted with 50 mM Tris/HCl buffer, pH 6.8, to a concentration of 175 mM NaCl, and subsequently is further purified by gel filtration on Sepharose® CL6B (Pharmacia). Gel filtration is effected by a linear flow of 5.7 cm/h in a column having a diameter of 26 mm and a bed height of 82 cm. The protein fraction of the exclusion volume is UV-spectroscopically detected at 280 nm. The protein peak of the exclusion volume is concentrated by ultrafiltration with an ultrafilter having a retention mass of 30,000 D. A thus produced von Willebrand factor/factor VIII complex has a specific activity of 173 Ristocetin cofactor units (U RCoF) vWF/mg protein (determined by protein determination according to Bradford, Anal. Biochem. 72:248–254, 1976). The preparation is free from coagulation factors II, VII, IX, X, XI and XII.

To immunize the goat, 2 mg of von Willebrand factor/factor VIII complex are emulsified with 0.5 ml of complete Freund's adjuvans and administered subcutaneously. Four weeks after the basic immunization, a booster is carried out with the same antigen amount, but emulsified in incomplete Freund's adjuvans. Blood samples from the goat are used to test the success of immunization. After a further four weeks after the booster, a second booster is carried out with the same amount of antigen, but immunization is effected intravenously. Subsequently, the inibitor plasma is recovered by plasmapheresis. A thus obtained plasma constitutes a high-titer von Willebrand factor inhibitor plasma, as will be explained in the following examples.

EXAMPLE 2

Immunabsorption of the inhibitor plasma.

To make the inhibitor plasma prepared according to Example 1 specific for von Willebrand factor, and to exclude a cross-reactivity with factor VIII which might also be present in the immunizing antigen complex, the plasma is absorbed with factor VIII. To this end, the plasma is incubated in equal volume portions with a highly purified factor VIII preparation (Kogenate®, Miles/Cutter, 100 U FVIII/ml) for 2 hours at 37° C. The precipitate formed is separated by centrifugation at 10,000 g for 10 minutes. The supernatant antibody-containing solution is free from cross-reactivity with factor VIII.

EXAMPLE 3

Alternative method of recovering an anti-vWF inhibitor plasma

Analogous to Example 1, a goat is immunized with von Willebrand factor.

The preparation of the immunizing antigen is performed as described in Example 1, yet with the following modification. After gel filtration and ultraconcentration of the von Willebrand factor complex, the latter is taken up in a buffer (50 mM glycine, 175 mM NaCl, 250 mM $CaCl_2$, pH 6.8) and further purified by renewed gel filtration over Sepharose®CL6B (Pharmacia) with a linear flow of 5.7 cm/h at 4° C. on a separating column having a diameter of 26 mm and a bed height of 82 cm. In doing so, von Willebrand factor and factor VIII are quantitatively dissociated and separated by the chromatographic separating medium. The protein peak of the exclusion volume detected by measurement of the UV absorption at 280 nm is collected and concentrated by ultrafiltration over a membrane having a retention mass of 30,000 D. The thus recovered von Willebrand factor preparation has a specific acitivty of at least 200 Ristocetin Cofactor (RCoF) U/mg protein and is free from coagulation factors II, VII, VIII, IX, X, XI and XII.

Immunization and recovery of the respective inhibitor plasma are performed as in Example 1.

EXAMPLE 4

In vitro characterization of von Willebrand factor inhibitor plasma

Von Willebrand factor inhibitor plasma produced according to Example 1 is assayed for its cross-reactivity with murine von Willebrand factor by incubating goat-anti von Willebrand factor inhibitor plasma with murine normal plasma produced from a pool from at least 10 healthy mice, at a concentration of 10 % by volume at 37° C. Prior to incubation, the goat plasma is heated at 56° C. for 1 hour so as to inactivate endogenously contained goat factor VIII which may interfere with the following test. Samples from the test mixture are taken immediately after mixing of the plasmas, as well as after 1 and 3 hours. Since a functional von Willebrand factor test is not available in mouse plasma, the instability of factor VIII during long-term incubation, which is due to the lack of von Willebrand factor, is assayed indirectly. The results can be seen in Table 1.

TABLE 1

| Mixture | | FVIII-content (%) | |
|---|---|---|---|
| Murine plasma + | Incubation time (h) | 2-stage clotting | chromogenic test |
| Goat-vWF- inhibitor plasma | 0 | 85 | 79 |
|  | 1 | 20 | 10 |
|  | 3 | 17 | 2 |
| Goat- normal plasma | 0 | 76 | 105 |
|  | 1 | 61 | 68 |
|  | 3 | 68 | 70 |

Normal murine plasma (=100%) contains 0.3 IU FVIII/ml, measured in the 2-stage test, and 0.6 IU FIII/ml, measured with a chromogenic factor VIII test (Immunochrom FVIII:C, Immuno). By incubating with the inhibitor plasma, the factor VIII activity decreases after 3 hours to approximately 2–17%, depending on the test method used. As the control, murine plasma is incubated with 10% by volume of goat normal plasma. There is no significant decrease of the FVIII concentration over time.

EXAMPLE 5

In vivo evaluation of von Willebrand factor inhibitor plasma in rabbits

White New Zealand rabbits (approximately 2 kg body weight, 6 months old) are anesthetized with ketamine hydrochloride (65 mg/kg) and xylazin (10 mg/kg). Anesthesia is maintained for the entire duration of the test by administering pentobarbital. The animals are placed in the supine position so that the hind paws come to lie on the side. Subsequently, the right femoral vene is dissected, and a venous entry is established for the continuous infusion of the test solutions by means of a Perfusor VI (Braun & Melsungen AG). Subsequently, the cuticle bleeding time is determined according to a modified method of Giles et al., Blood 60:727–730, 1982. For this purpose, the fur surrounding the claw was shaved to avoid blood emerging at the later bleeding from being absorbed by the fur. The cuticle is injured by means of a nail clipper. Immediately thereafter, a filter (Pipetman P5000 protective filter, Gilson) was established below the wound such that blood can drip directly onto the filter without creating suction caused by a capillary effect, so as to prevent a forming blood clot from being damaged. The filter units were changed every 2 minutes, and the emerging blood was collected in fractions. Blood was continued to be collected for 30 minutes. If the bleeding had not stopped by then, the wound was cauterized. Various claws can be used in one and the same animal. As the internal control, bleeding prior to the administration of the inhibitor plasma is tested in each case.

Figure 1:
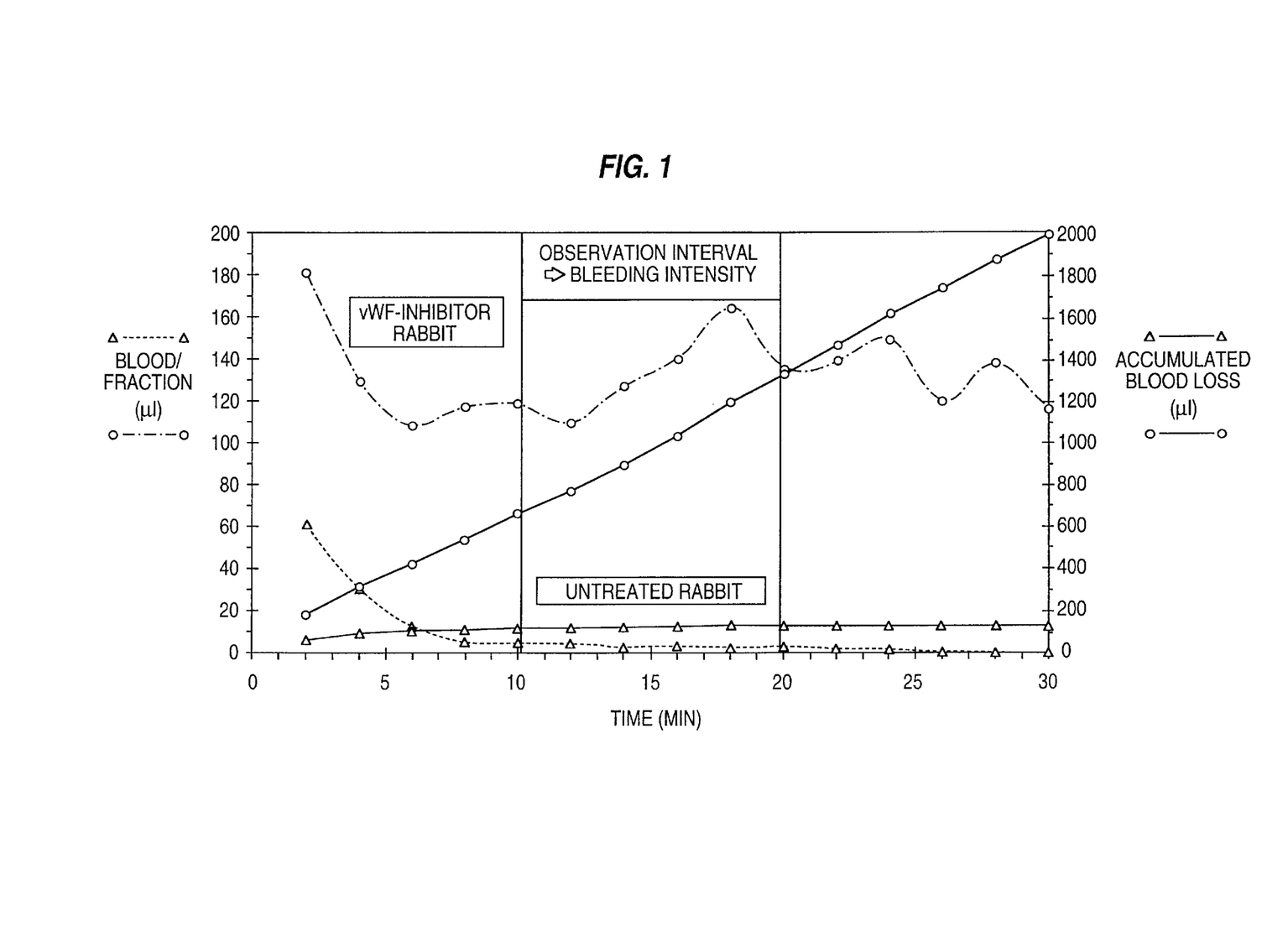
FIG. 1 shows the mean value of the bleeding characteristics of normal rabbits (Δ, n=92) as compared to rabbits which had been treated with von Willebrand factor inhibitor plasma (o, n=11), the curves depicted in broken lines indicating the blood loss per time unit, and the curves depicted in solid lines indicating the accumulated blood loss, the observation interval for determining the bleeding intensity being between 10 and 20 min.

Bleeding characteristics are qualified by extraction of the blood collected in fractions on the filters with respective 5 ml portions of 0.04% ammonium hydroxide solution for 5 hours. Thus, the erythrocytes collected with the blood in the filter are lysed. By a 10 minute sonication (Sonorex RK 100, Bandelin electronic, Berlin) the hemoglobin is extracted and quantitatated photometrically at 416 nm against a calibration curve. A calibration curve can be determined by pipetting rabbit blood volumes of between 10 $\mu$l and 1 ml onto filters, extracting the same as described above, and photometrically determining the hemoglobin at 416 nm. Accordingly, linear calibration curves can be established, which allow for a direct computing of the hemoglobin concentration to the amount of blood per filter. The bleeding characteristics of the cuticle cutting are determined by graphically plotting the amount of blood in each 2 minute fraction against time (FIG. 1). To evaluate the bleeding characteristics, furthermore the accumulated blood loss is determined by entering in the graph the individual blood fractions additively against time (cf. FIG. 1). The slope for the interval of the cumulative bleeding curve between 10 and 20 minutes is used as a relevant bleeding criterion. This value is independent of the initial amount of blood, which may vary due to poorly standardizable nail cutting techniques. The slope of these bleeding curves in the 10–20 minute observation interval serves as a measure of bleeding intensity. A slope equal to 0 indicates that bleeding has stopped; a slope greater than zero with a correlation coefficient >0.8 indicates constant bleeding. Normal rabbits tested under these conditions do not exhibit any bleeding in this observation interval, i.e. the bleeding has already stopped before.

Analogous thereto, rabbits are infused with von Willebrand factor inhibitor plasma prepared according to Example 1 or Example 3, at a concentration of 0.5 ml/kg body weight. After infusion of the inhibitor plasma, the animals exhibit a bleeding rate of 30–110 $\mu$l blood/min in the observation period, with a correlation coefficient of the bleeding curve of >0.9.

EXAMPLE 6

In vivo evaluation of the inhibitor plasma in mouse.

Figure 2:
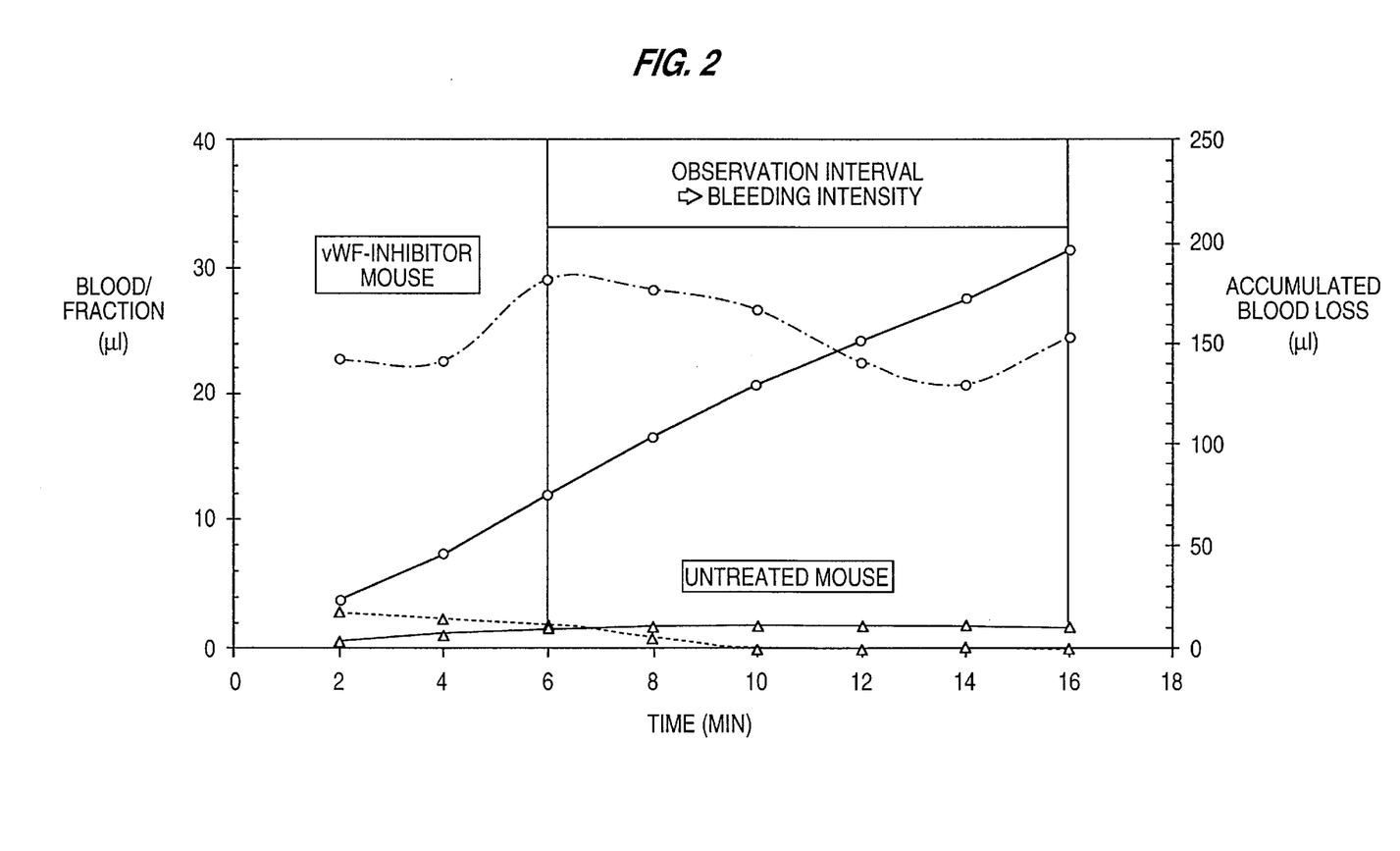
FIG. 2 shows the mean value of the bleeding characteristics of normal mice (Δ, n=10) as compared to mice previously treated with von Willebrand factor inhibitor plasma (o, n=10), the curves depicted in broken lines indicating the blood loss per time unit, and the curves depicted in solid lines depicting the accumulated blood loss, the bleeding intensity having been determined at an observation interval of between 6 and 16 minutes.

Female NMRI-mice (20–30 g) are used and anesthetized by administration of 63 mg/kg pentobarbital. Subsequently, the bleeding characteristics are determined with a modified method according to Novak et al., Br. J. Haematol. 69:371–378, 1988, by a defined injury of the tail tip. As described in Example 5, blood emerging from the arteriovenous injury is collected on filters and quantitated analogous to Example 5. In contrast to the rabbits, several nails are available for cutting, here no internal control can be carried out in relation to the normal bleeding behaviour. Therefore, a control group of mice is treated with an 0.9% NaCl solution (2 ml/kg body weight). The bleeding characteristics of the control group can be seen in FIG. 2. There, the measured period of time is 16 minutes, the observation interval is between 6 and 16 minutes. In the observation interval, untreated mice have a bleeding rate of <0.01 µl blood/min. Analogous to Example 5, mice are treated with 10 ml/kg anti-von Willebrand factor inhibitor plasma, and subsequently the bleeding behaviour is quantitated. Mice treated with von Willebrand factor inhibitor plasma according to Example 1 or 3 have bleeding rates of 4–19 µl blood/min. The correlation coefficient of the curve defining the bleeding characteristics lies at >0.8. After the test has been finished, blood is drawn from the mice by heart puncture, admixed with citrate, and plasma is recovered. From this plasma the structure of von Willebrand factor is determined according to the method of Ruggeri et al., Blood 57:1140–1143, 1981. Therein, von Willebrand factor multimers are determined by immunoenzymatic staining according to Aihara et al., Thromb.Haemostas. 55: 263–267, 1986. As the primary antibody, a rabbit anti-human von Willebrand factor antiserum (Dakopatts) in a dilution of 1:5,000 is used. As the secondary antibody, an alkaline phosphatase conjugated affinity-purified goat anti-rabbit IgG (H+L) antibody (Axell, Accurate Chemical and Scientific Corp., NY) in a dilution of 1:1,000 is used. Staining of the protein bands is effected by m eans of the nitroblue tetrazolium chloride/bromochloroindolyl phosphate substrate system.

Under these test conditions, murine normal plasma has a characteristic von Willebrand factor multimer structure. Upon administration of von Willebrand factor inhibitor, in 3 out of a series of 5 examined mice von Willebrand factor could no longer be detected. In 2 out of 5 animals, the von Willebrand factor content is clearly reduced, von Willebrand factor multimers are only weakly visible.

EXAMPLE 7

Figure 3:
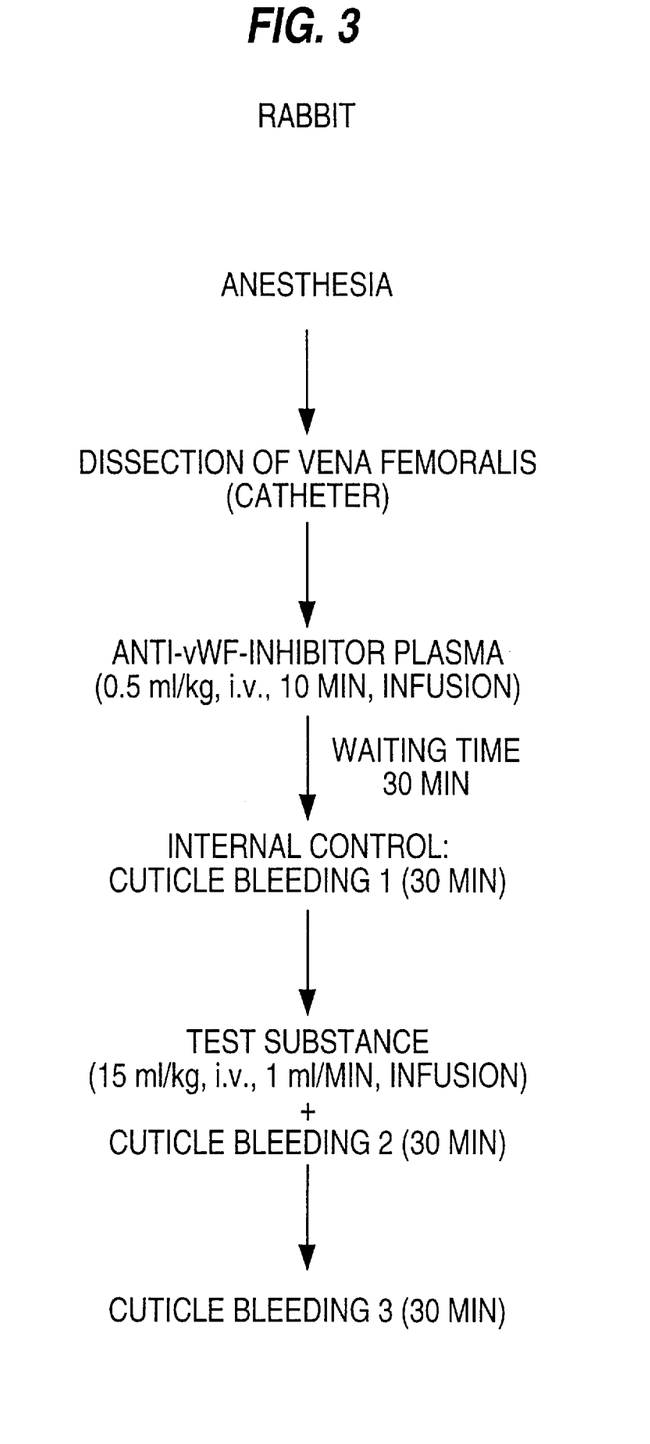
FIG. 3 gives the protocol for testing the effect of FEIBA in von Willebrand factor inhibitor rabbits.
Figure 4:
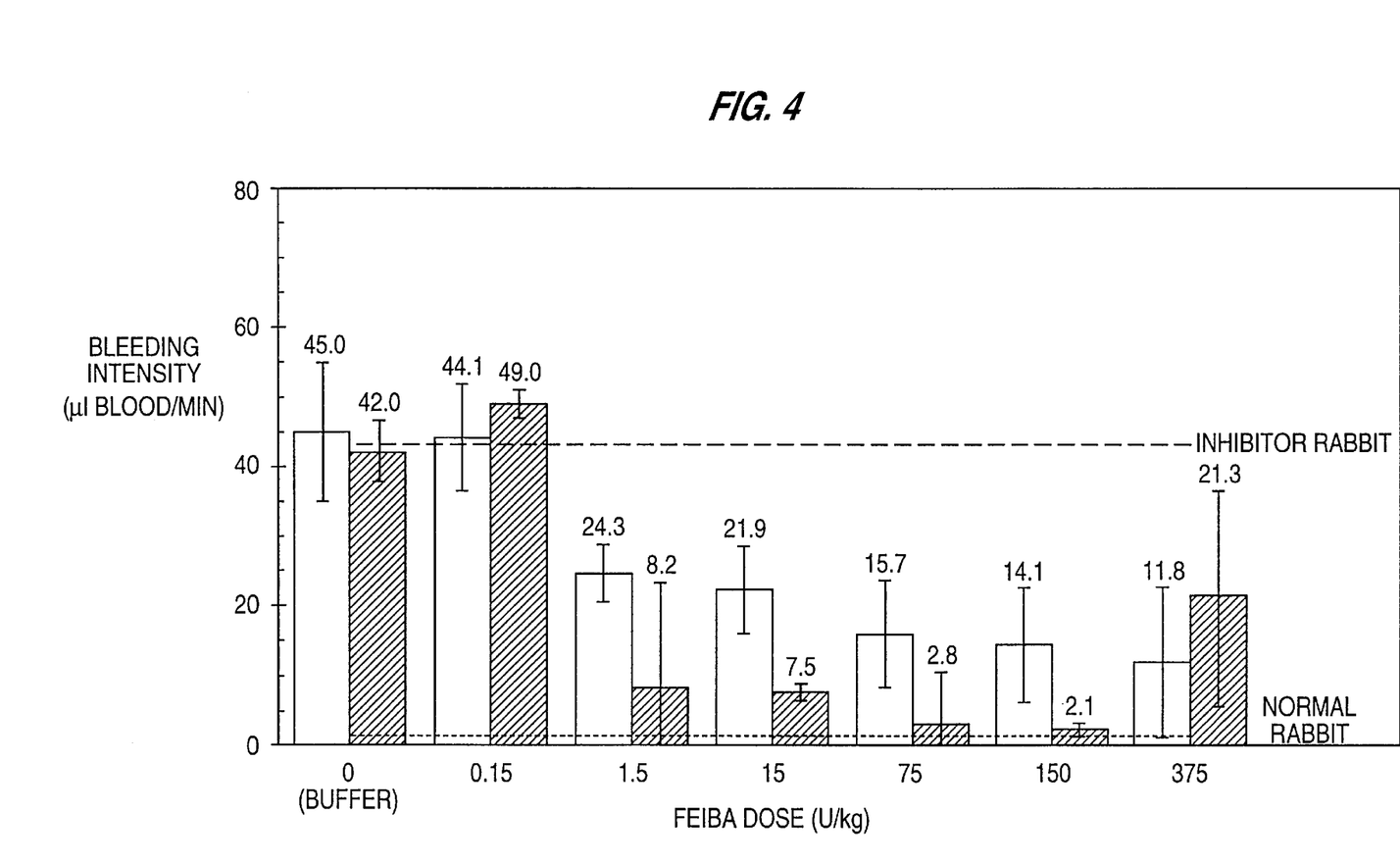
FIG. 4 shows the bleeding intensities of von Willebrand factor inhibitor rabbits treated with increasing doses of FEIBA, the control group having received buffer as a comparison (broken line: mean value of 33 von Willebrand factor inhibitor rabbits ± standard deviation; dotted line: mean value ± standard deviation of 92 normal rabbits)

Testing of the efficacy of FEIBA in rabbits pre-treated with von Willebrand factor inhibitor The test protocol can be taken from FIG. 3. Rabbits received 0.5 ml/kg von Willebrand factor inhibitor plasma prepared according to Example 1. FEIBA S-TIM4, Immuno (1,000 U) was reconstituted with 20 ml A. dest. Upon complete dissolution of the substance, the latter was diluted with citrated buffer (4 g $Na_3$.citrate, 1.8 g NaCl, pH 7.0), and the rabbits were infused with 30 ml of the respective dilutions at an infusion rate of 1 ml/min, at doses of 0.15, 1.5, 15, 75, 150 and 375 U/kg. The bleeding characteristics were determined in parallel with the substance infusion and 30 minutes after the start of the FEIBA infusion, as described in Example 5. FIG. 4 shows the median of the bleeding intensity in the observation interval of 6 rabbits/group. The bleeding intensity of the cuticle bleeding carried out simultaneously with substance infusion showed a dose-dependent reduction with a maximum at 375 U/kg. When FEIBA infusion had been stopped, the bleeding characteristics showed an intensity optimum between 75 and 150 U/kg. The results at this dose range do not differ from the bleeding behaviour of untreated rabbits. At a dose of 375 U/kg, the hemorrhagic effect is increased again. This result shows that according to the indication, an effect caused by a coagulation inhibitor can be neutralized with FEIBA. The dose of 50–100 U FEIBA/kg recommended as the optimum effective dose for bleeding in human application is confirmed by this model. Thus, the relevance of the rabbit animal model with von Willebrand factor inhibitor is demonstrated.

EXAMPLE 8

Figure 5:
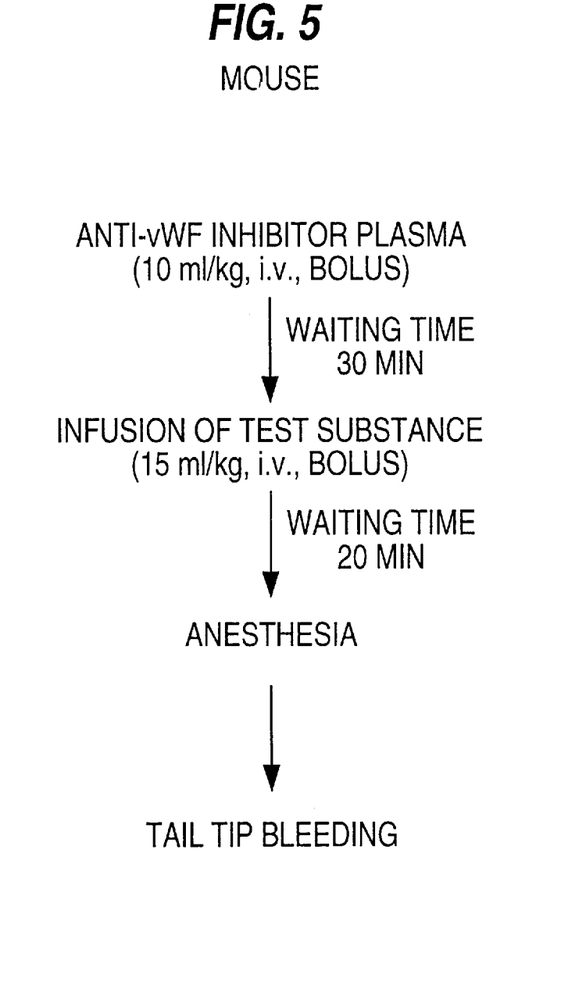
FIG. 5 shows the protocol for testing IMMUNATE® or recombinant von Willebrand factor in von Willebrand factor inhibitor mice.

Effect of a factor VIII/von Willebrand factor complex in mice pre-treated with von Willebrand factor inhibitor plasma The test protocol can be taken from FIG. 5.

Figure 6:
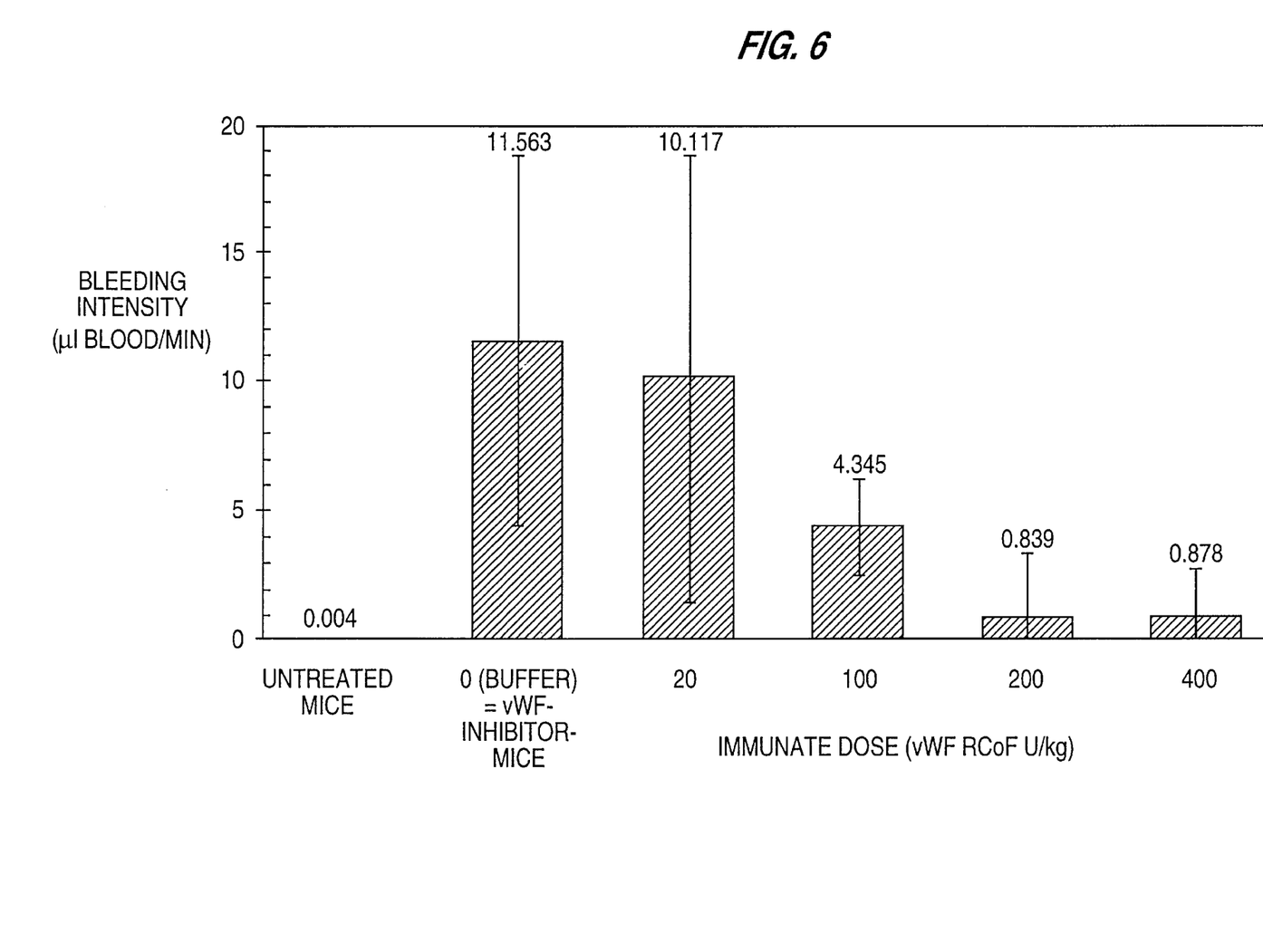
FIG. 6 shows the bleeding intensities of normal mice, mice previously treated with von Willebrand factor inhibitor and the dose/response relationship of the bleeding intensity of von Willebrand factor inhibitor mice after the addition of increasing doses of factor VIII/von Willebrand factor complex (IMMUNATE®)

Mice were pre-treated with the anti-von Willebrand factor inhibitor described in Example 3, at a dose of 10 ml/kg body weight. FIG. 6 shows that the bleeding intensity of a group of 10 mice pre-treated with anti-von Willebrand factor inhibitor plasma has a mean of 11.6 µl blood/min. In comparison thereto, untreated mice exhibit a bleeding intensity of 0.004 µl/min in the observation interval. Immunate S-TIM4, Immuno (250 U/bottle) was reconstituted with A. dest. according to the manufacturer's instructions, so that the solution contained 10.9 Ristocetin-cofactor units (U RCoF) vWF/ml and 50 IU FVIII/ml. At a constant dose volume of 20 ml/kg body weight, the mice were infused with doses of 20, 100, 200 and 400 Ristocetin cofactor units (U RCoF) vWF/kg body weight. FIG. 6 shows the bleeding intensity of the mean value of 10 animals/group each. The bleeding intensity could be reduced dose-dependently, and with 200 Ristocetin cofactor units (U RCoF) vWF/kg body weight, the bleeding behaviour of the hemorrhagic mice could nearly be normalized. Multimer analysis, which was carried out as described in Example 5, on plasma samples of von Willebrand factor-inhibited mice after Immunate administration shows that the von Willebrand factor that could compensate the abnormal bleeding inclination was the infused human von Willebrand factor/factor VIII complex, and not the endogenous murine von Willebrand factor which could have been liberated from the immune complexes. Thus, the efficacy of the model for evaluating substances utilized with von Willebrand factor inhibitors has been demonstrated.

EXAMPLE 9

Figure 7:
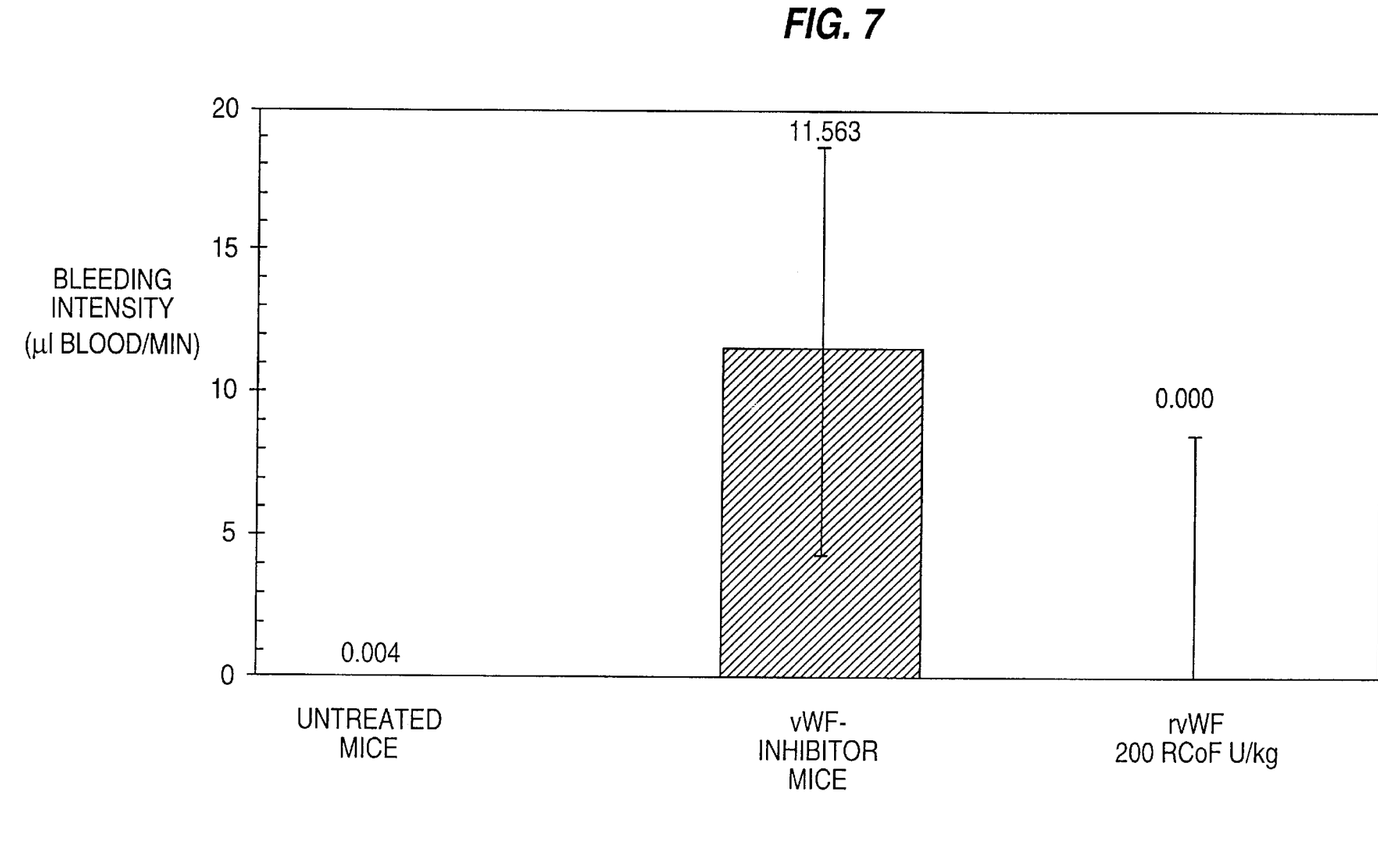
FIG. 7 shows the bleeding intensities of von Willebrand factor inhibitor mice after administration of recombinant von Willebrand factor (200 RCoF U/kg) as compared to normal mice and of von Willebrand factor inhibitor mice.

Effect of a recombinant von Willebrand factor preparation in mice pre-treated with von Willebrand factor inhibitor plasma Analogous to Example 8, mice were treated with a recombinant human von Willebrand factor recovered from CHO cells, at a dose of 200 Ristocetin cofactor units (U RCoF) rvWF/kg body weight. FIG. 7 shows the bleeding characteristics of untreated mice as compared to von Willebrand factor inhibitor-pretreated animals which were treated with recombinant von Willebrand factor. By administering 200 Ristocetin Cofactor units (U RCoF) rvWF/kg body weight, the abnormal bleeding behaviour of von Willebrand factor inhibitor mice could be corrected to that of healthy mice. By using a pure recombinant preparation of von Willebrand factor protein which cannot be contaminated by other plasma proteins by the nature of its origin, it is confirmed that the model is a von Willebrand factor-specific animal model.

What is claimed is:

1. A method of generating a mammalian blood clotting disorder model comprising administering an effective amount of a polyspecific anti-plasma antibody preparation to a non-human mammal, wherein several blood factors are functionally inhibited and/or eliminated in said non-human mammal thereby changing the blood clotting time when compared to a non-human mammal that has not received said polyspecific anti-plasma antibody preparation.

2. The method as set forth in claim 1, further comprising administering at least one blood factor, which was inhibited and/or eliminated by said polyspecific anti-plasma antibody preparation, whereby the changed clotting blood time is only dependent on a deficiency of at least one blood factor which has not been administered.

3. A method of evaluating substances for treating blood clotting disorders, comprising administering a polyspecific anti-plasma antibody preparation to a non-human mammal, wherein said antibody preparation inhibits and/or eliminates several blood factors and results in a blood clotting disorder in said non-human mammal; administering said substance to be evaluated to said non-human mammal; and determining the change of at least one blood clotting parameter of said mammal by said substance to be evaluated.

* * * * *